US00PP33109P2

(12) United States Plant Patent
Olesen

(10) Patent No.: US PP33,109 P2
(45) Date of Patent: Jun. 1, 2021

(54) MINIATURE ROSE PLANT NAMED 'POULPAH100'

(50) Latin Name: *Rosa hybrida*
Varietal Denomination: Poulpah100

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 16/873,987

(22) Filed: Sep. 3, 2020

(51) Int. Cl.
*A01H 5/02* (2018.01)
*A01H 6/74* (2018.01)

(52) U.S. Cl.
USPC ..... Plt./116

(58) Field of Classification Search
USPC ..... Plt./101, 116, 117
See application file for complete search history.

(56) References Cited

PUBLICATIONS

Poulsen Roser website: Novelties IPM 2016 (http://www.poulsenroser.com/news/exhibitions/ipm-2016/novelties-ipm-2016.aspx) retrieved Nov. 20, 2020. 4 pages. (Year: 2020).*

* cited by examiner

*Primary Examiner* — Susan McCormick Ewoldt
*Assistant Examiner* — Karen M Redden

(57) ABSTRACT

A new garden rose plant of the Miniature class which has abundant, green white flowers and attractive foliage. This new and distinct variety has shown to be uniform and stable in the resulting generations from asexual propagation.

2 Drawing Sheets

Botanical designation: *Rosa hybrida.*
Variety denomination: 'Poulpah100'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2012 and the resulting seeds were planted in a controlled environment in Fredensborg, Denmark. The new variety, named 'Poulpah100', originated as a single seedling from the stated cross.

The new variety may be distinguished from its male pollen parent and female seed parent primarily by the following characteristics. The male pollen parent plant has pure white flowers while the new variety has white flowers with other intonations of green white. The female seed parent plant has white flowers with other intonations of orange white while the new variety has white flowers with other intonations of green white.

The objective of the hybridization of this rose variety was to create a new and distinct variety with unique qualities, such as:

1. Uniform and abundant green white flowers;
2. Vigorous, but compact growth when propagated on its own roots;
3. Exceptional disease resistance.

This combination of qualities is not present in previously available commercial cultivars of this type, known to the inventor, and distinguish 'Poulpah100' from all other varieties of which we are aware.

As part of the rose development program, Mogens N. Olesen germinated the seeds from the aforementioned hybridization during winter of 2012 and conducted evaluations on the resulting seedlings in a controlled environment in Fredensborg, Denmark. 'Poulpah100' was selected in the spring of 2013 by the inventor as a single plant from the progeny of the aforementioned hybridization.

Asexual reproduction of 'Poulpah100' by rooted cuttings was first done by Mogens N. Olesen in the nursery in Fredensborg, Denmark in July, 2013. This initial and other subsequent asexual propagations conducted in controlled environments have demonstrated that the characteristics of 'Poulpah100' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah100'.

Specifically illustrated in FIG. 1 of the drawings are open flowers viewed from above and the side, petals detached revealing reproductive flower parts and receptacle, and flower buds as the sepals begin to divide.

Figure 1:
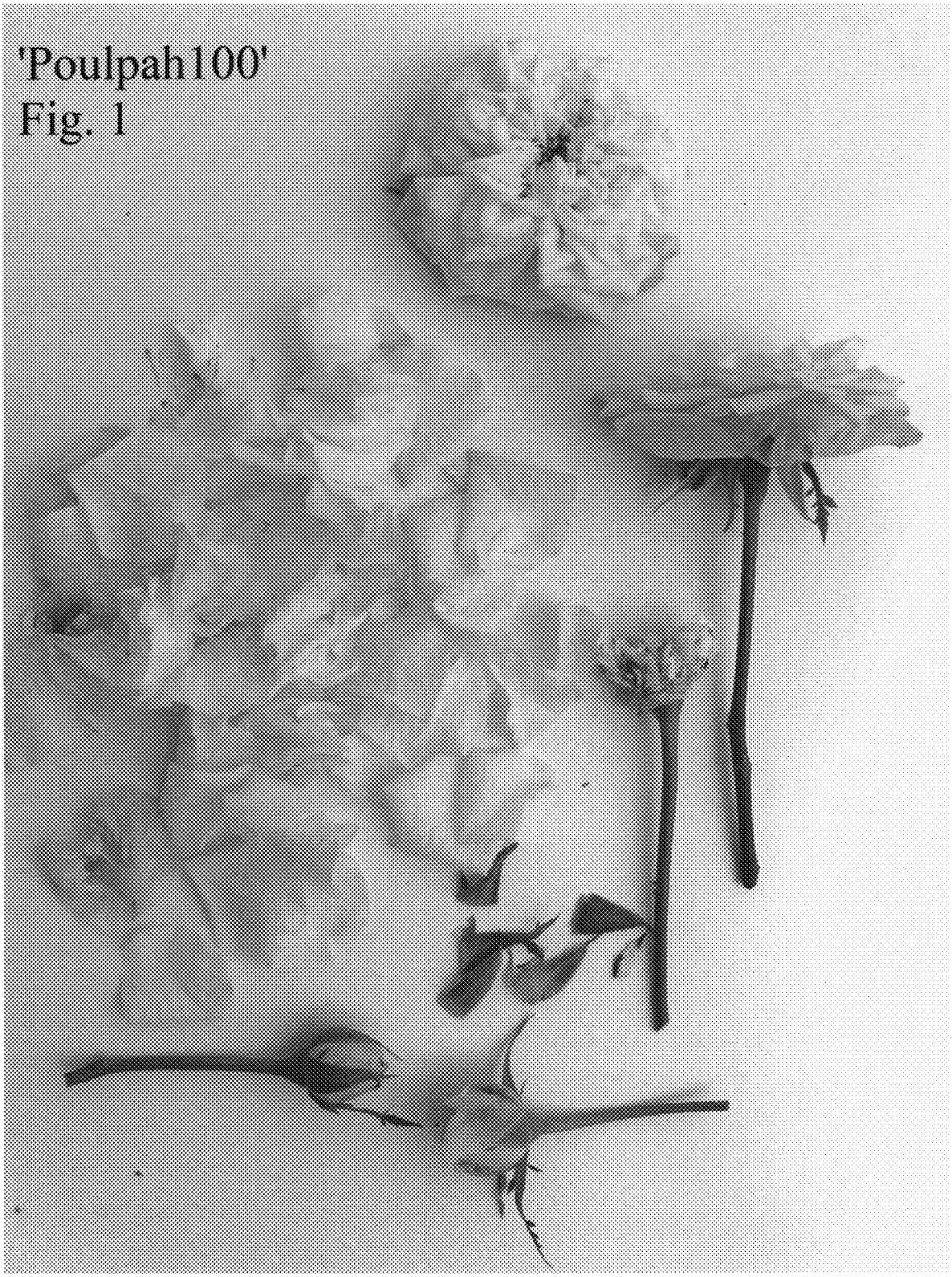
Figure 2:
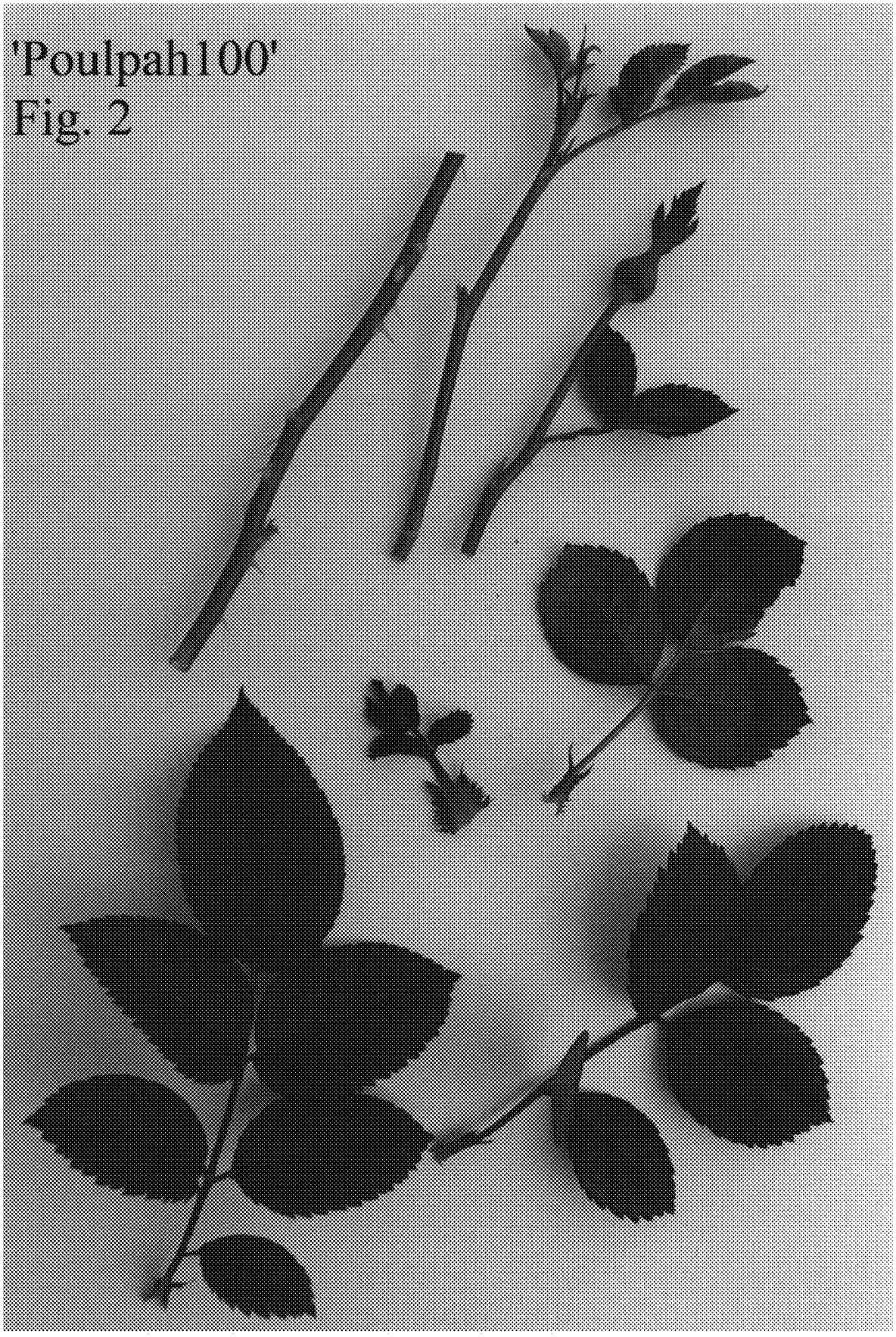

Specifically illustrated in FIG. 2 of the drawings are mature leaves, juvenile leaves exhibiting anthocyanin, and bare stems. Plants shown are 4 months of age.

DETAILED DESCRIPTION OF THE VARIETY

The following is a description of 'Poulpah100', as observed in its growth in a controlled environment greenhouse in Odense Denmark. Observed plants are 4 months old and were grown on their own roots in 19 cm containers. Color references are made using The Royal Horticultural Society (London, England) Colour Chart, 2001, except where common terms of color are used.

For a comparison, several physical characteristics of the rose variety 'Poulpah051', U.S. Plant Pat. No. 24,222 are compared to 'Poulpah100' in Chart 1.

CHART 1

| | 'Poulpah100' | 'Poulpah051' |
|---|---|---|
| Petal Count | 78 | 50 |
| Flower Diameter | 67 mm | 35 to 40 mm |
| General Tonality of Flower Color | Green-White Group 157D | White Group 155A with intonations of Green-White Group 157A |

FLOWER AND FLOWER BUD

Blooming habit: Continuous.

Flower bud:

*Size.*—Upon opening, 25 mm in length from base of receptacle to end of bud. Bud diameter is 17 mm.

*Bud form.*—Flat based ovoid.

*Bud color.*—As sepals divide petals are Yellow-Green Group 150D with intonations of Greyed-Red Group 180C.

*Sepal inner surface.*—Color: Yellow-Green Group 146D. Surface: Lightly pubescent.

*Sepal outer surface.*—Color: Yellow-Green Group 144A with intonations of Greyed-Red Group 179A at the apex of some sepals. Texture: Smooth.

*Sepal shape.*—Apex: Cirrhose. Base: Flat at union with receptacle.

*Sepal margin.*—Margins have moderate to strong foliaceous appendages on three of the five sepals.

*Sepal size.*—27 mm long, 9 mm wide.

*Receptacle.*—Texture: Smooth. Size: 6 mm in height, 9 mm wide. Color: Yellow-Green Group 144A. Shape: Funnel.

*Pedicel.*—Surface: Smooth. Length: 55 to 70 mm. Diameter: About 3.5 mm on average. Color: Yellow-Green Group 144A. Strength: Strong.

Flower bud development: Flower buds are borne single, or in clusters of 3 flower buds per stem.

Flower bloom:

*Fragrance.*—Light floral scent.

*Duration.*—The blooms have a duration on the plant of approximately 20 days. Petals fall cleanly away from plant after flowers have fully matured.

*Size.*—Flower diameter is 67 mm when open. Flower depth is 25 mm.

*Flower shape.*—Rosette very double flower with many slightly overlapping petals of different sizes.

*Shape of flower, side view.*—The upper portion is convex. The lower portion is concave.

Petalage: Under normal conditions, flowers have about 78 petals.

General tonality of flower: Open flowers are Green-White Group 157D.

Petal color:

*Upon opening, outer petals.*—Upper surface: Yellow-Green Group 145D at marginal zone. At the middle zone Green-White Group 157D. Lower surface: Yellow-Green Group 145D.

*Upon opening, inner petals.*—Upper surface: Green-White Group 157D. Lower surface: Green-White Group 157D.

*Basal petal spots.*—No distinctive coloration at the petal base observed.

*After opening, outer petals.*—Upper surface: Yellow-Green Group 145D at marginal zone. At the middle zone Green-White Group 157D. Lower surface: Yellow-Green Group 145D.

*After opening, inner petals.*—Upper surface: Green-White Group 157D. Lower surface: Green-White Group 157D.

*Basal petal spots.*—After opening no distinctive coloration at the petal base observed.

Petals:

*Petal reflex.*—Strong.

*Margin.*—Entire and uniform. No undulation.

*Shape.*—Rounded. Apex shape: Rounded. Base shape: Obtuse.

*Size.*—36 mm (l)×34 mm (w).

*Texture.*—Smooth to reticulate.

*Thickness.*—Thick.

Petaloids:

*Size.*—15 mm (l) by 15 mm (w).

*Quantity.*—5 to 8.

*Shape.*—Round, with an obtuse base and rounded or emarginate apex.

*Color.*—Green-White Group 157D with occasional streaks of Yellow-Green Group 145C on upper and lower surface.

Reproductive flower parts:

*Pollen.*—None observed.

*Anthers.*—Size: 2 mm in length. Color: Yellow-White Group 158A. Quantity: 20 on average.

*Filaments.*—Color: White Group 155A. Length: 3 mm.

*Pistils.*—Length: 9 mm. Quantity: 18 on average.

*Stigmas.*—Color: Greyed-Yellow Group 160B.

*Styles.*—Color: Green-White Group 157A.

*Location of stigmas.*—Level in location relative to the length of the filaments and the height of the anthers.

*Hips.*—None Observed.

PLANT

Plant growth: Upright. Plants are about 40 cm in height, and 38 cm wide.

Stems:

*Color of juvenile growth.*—Yellow-Green Group 144B.

*Color of mature growth.*—Yellow-Green Group 144A.

*Length.*—Canes are about 33 cm from the base of the plant to the flowering portion.

*Diameter.*—About 4 to 5 mm.

*Internodes.*—On mature canes about 37 to 50 mm between nodes.

*Surface texture.*—Young wood: Smooth. Older wood: Smooth.

Long prickles:

*Incidence.*—4 to 5 prickles per 10 cm of stem.

*Size.*—Average length of prickles on mature stems is 10 mm.

*Shape*.—Upper portion is linear. Lower portion is deep concave.

*Color*.—Juvenile prickles: Greyed-Yellow Group 160D. Mature prickles: Greyed-Yellow Group 160D.

Plant foliage:

*Compound leaf*.—About 140 mm (l)×92 (w).

*Quantity*.—2 or 3 leaves per 10 cm of stem on average.

*Leaf bearing angle to the stem*.—45 degrees.

*Color of juvenile foliage*.—Upper side: Yellow-Green Group 144A with strong intonations of Greyed-Purple Group N186C. Lower side: Greyed-Purple Group 183B.

*Color of mature foliage*.—Upper side: Yellow-Green Group 147A. Lower side: Yellow-Green Group 147B.

Plant leaves and leaflets:

*Stipules*.—Size: 11 mm long, 5 mm wide. Quantity: 2 per compound leaf. Shape: Linear, slightly broad based with outward extending apices. Margins: Finely serrated. Color: Yellow-Green Group 144A.

*Petiole*.—Length: 25 mm. Diameter: 2 mm. Upper surface color: Yellow-Green Group 146A. Lower surface color: Yellow-Green Group 144A.

*Rachis*.—Length: 43 mm. Upper surface color: Yellow-Green Group 146A. Lower surface color: Yellow-Green Group 144A.

*Leaflet*.—Quantity: Normally 5 to 7 leaflets. Margins: Serrated. Size: Terminal leaflets are about 61 mm long, 43 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpah100', substantially as illustrated and described herein, due to its abundant green white flowers, disease resistance, and extended period of bloom.

* * * * *

'Poulpah100'

'Poulpah100'